United States Patent [19]

Finley et al.

[11] Patent Number: 4,838,081
[45] Date of Patent: Jun. 13, 1989

[54] METHOD AND APPARATUS FOR IMPROVING THE RELIABILITY FOR DOUGH TESTING RESULTS

[75] Inventors: John W. Finley, Whippany; Hamed A. Faridi, Lake Hiawatha, both of N.J.

[73] Assignee: Nabisco Brands, Inc., Parsippany, N.J.

[21] Appl. No.: 161,137

[22] Filed: Feb. 26, 1988

Related U.S. Application Data

[63] Continuation of Ser. No. 834,369, Feb. 28, 1986, abandoned.

[51] Int. Cl.⁴ .......................................... G01N 33/10
[52] U.S. Cl. .......................................... 73/169
[58] Field of Search .......................................... 73/169

[56] References Cited

U.S. PATENT DOCUMENTS

| | | | |
|---|---|---|---|
| 1,468,900 | 9/1923 | Chopin | 73/169 |
| 1,591,360 | 7/1926 | Chopin | 73/169 |
| 2,275,341 | 3/1942 | Brabender | 73/169 |
| 2,281,182 | 4/1942 | Chopin | 73/76 |
| 2,673,463 | 3/1954 | Kimball et al. | 73/169 |
| 3,160,002 | 12/1964 | Lovette | 73/787 |
| 3,169,395 | 2/1965 | Enoch et al. | 73/169 |
| 3,894,828 | 7/1975 | Moline et al. | 425/373 |
| 4,046,920 | 9/1977 | Moline | 426/19 |
| 4,272,824 | 6/1981 | Lewinger et al. | 177/50 |
| 4,334,447 | 6/1982 | Martin et al. | 83/111 |
| 4,564,703 | 1/1986 | Garbar et al. | 73/169 |
| 4,565,089 | 1/1986 | Arciszewski et al. | 73/169 |

FOREIGN PATENT DOCUMENTS

| | | | |
|---|---|---|---|
| 733686 | 10/1932 | France | 73/169 |
| 115865 | 7/1926 | Switzerland | 73/169 |

OTHER PUBLICATIONS

Measurement And Controls, vol. 3, Nov. 1970 (73/169), "An In-Line Consistency Meter For Doughlike Materials", Babb, A. T. S. et al.

Primary Examiner—William A. Cuchlinski, Jr.
Assistant Examiner—W. Morris Worth
Attorney, Agent, or Firm—Richard Kornutik

[57] ABSTRACT

An apparatus and method improves the reliability and reduces the variability of test results using a Alveographe testing appartus for dough. Dough samples are prepared and the qualities of the flour and/or doughs used are measurable by biaxially stretching dough samples until they burst employing air pressure for the biaxial deformation. The reliability and reduced variability of test results is achieved by using a low-friction coating on the surfaces of the tools and equipment used to prepare the dough samples. The standard deviation is thereby reduced by approximately one-half. In particular, the low friction coating used is polytetrafluoroethylene.

7 Claims, 2 Drawing Sheets

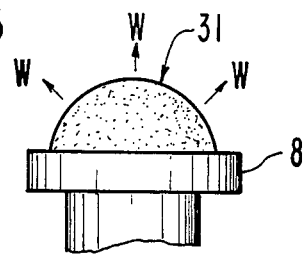
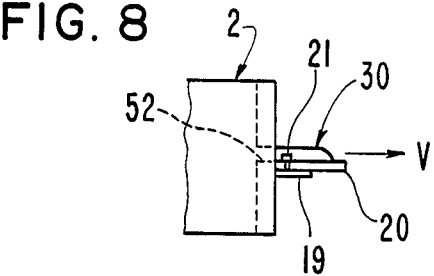
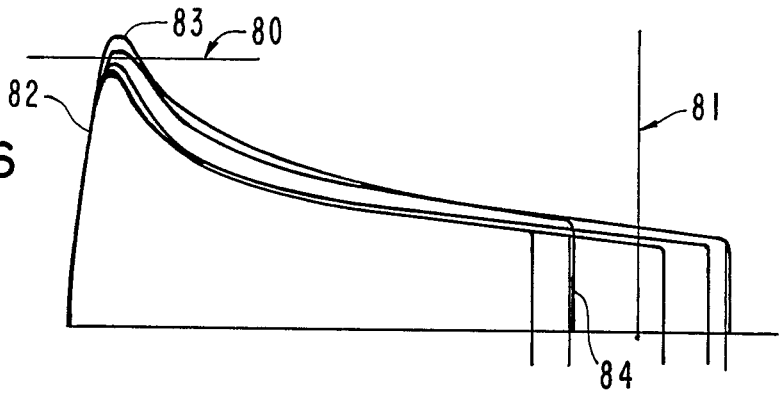
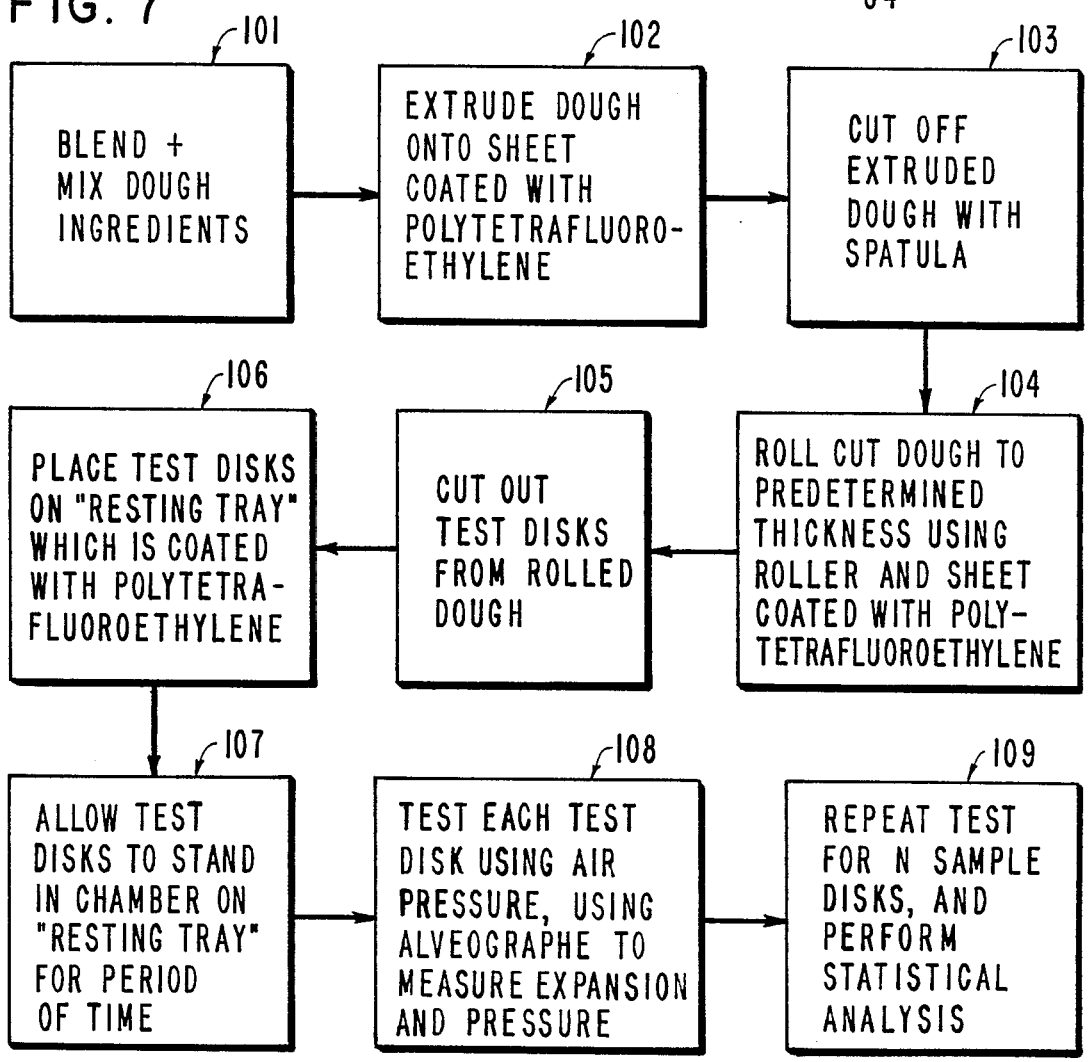

METHOD AND APPARATUS FOR IMPROVING THE RELIABILITY FOR DOUGH TESTING RESULTS

This is a continuation application of application Ser. No. 834,369 filed Feb. 28, 1986 now abandoned.

BACKGROUND OF THE INVENTION

1. Technical Field Of The Invention

This invention relates generally to dough testing devices and methods. In particular, this invention relates to an apparatus and method for testing dough qualities and characteristics in a reliable and repeatable manner.

Dough testing equipment using burst testing is generally known in the mechanical arts.

2. Background Art

A particular apparatus for burst testing of doughs is, for example, the Chopin Alveographe. This device is a mechanical dough testing apparatus used for determining quality of wheats and of flours. It also tests the rheological characteristics of dough. The principle of this device is based upon bi-axial stretching of a dough sample, which under pressure expands into a large volume bubble having a very thin wall. This type of stretching emulates the deformation of the dough under the influence of gaseous pressure of biological origin, such as carbonic fermentation using yeast, or chemical origin, employing chemical yeasts.

In such an alveographe, the internal bubble pressure is recorded, that is, the air or other fluid pressure existing inside the bubble. The volume of the bubble is also measured. A particular dough, employing particular flours, can be tested according to this device, and the test results after repeated test measurements of the dough result in a close correllation between the measurements obtained and the baking results of such a dough. Therefore, this prior art device is useful in evaluating particular wheat varieties for use in dough, for evaluating particular doughs and formulations of doughs, and for testing the quality of a particular flour.

Due to inherent testing errors in the Alveograph, the measured variables for each dough sample can vary even for a highly uniform batch of dough samples. Furthermore, a large number of tests must generally be conducted in order to determine a "true" value for the dough characteristics being measured by this device, employing a statistical analysis. Such statistical analysis includes a determination of standard deviation of the measured values about some average value. Thus, the smaller the standard deviation, the greater the likelihood that the average value about which the standard deviation occurs is the true value of the variable being measured.

U.S. Pat. No. 3,160,002 to Lovette shows an automatic burst tester. This particular burst tester has graphical output as seen in FIGS. 1 and 3. An air supply as seen in FIG. 4 is used to provide the bursting pressure.

In U.S. Pat. No. 4,272,824 to Lewinger et al., a batch of ingredients is mixed in a receptacle, the mixed batch is then divided into equal portions, and weight is measured. A control device is shown for adjusting a portion of the mixed batch to be transferred, including a dividing means.

U.S. Pat. No. 2,673,463 to Kimball et al., teaches a device for determining the consistency of materials. This is particularly with reference to the mixing of dough, wherein a sample dough is made, and kneaded until an adequate consistency is reached. This patent takes note that the hygroscopic propeties of flour may vary from sack to sack, and that other controls and testing devices may be somewhat inaccurate, and that human errors also occur. A power graph is employed in this invention to aid in providing repeatable test results.

U.S. Pat. No. 2,275,341 to Braybender relates to a device for testing dough. In this device, as seen in FIG. 4, a curve is made representing the resistence to extension of the dough with respect to the extensibility of the dough. The dough is tested until it reaches a breaking point. Here, a dough sample is ruptured by an arm of a machine.

A variety of patents relating to dough testing include U.S. Pat. Nos. 1,591,360; 1,468,900; and 2,281,182. These patents are each by Chopin. Also, a French Patent to Chopin No. 733,686 relates to such testing equipment for determining properties of materials. All of these references are deemed relevant to Alveograph.

SUMMARY OF THE INVENTION

By the present invention, the variability of test results in burst-testing type of apparatus is greatly reduced and the standard deviation of test results of a single mixed batch of dough is reduced as compared to the prior art testing devices, thereby increasing significantly the reliability of the test results obtained.

The present invention employs, preferably, a Chopin Alveograph for burst-testing of dough samples. The dough samples are first made by mixing the desired ingredients thoroughly and then extruding them through a slot onto a shelf having a coating of polytetrofluorethylene, which coating is known by a commercial name as Teflon ®.

The extruded dough sample is then placed upon a flat surface having upstanding sidewalls of a predetermined height, the flat surface also being coated with polytetrafluorethylene, also known commercially as Teflon ®. A roller is used having arms which span the upstanding sidewalls of the support tray, so that the roller extends below the predetermined height of the sidewalls such as that during a rolling operation, a dough sample placed beneath the roller will eventually be rolled to a very uniform thickness, which thickness does not vary significantly from one dough sample to another, except at the edge portions thereof. The roller surface itself is preferably coated with polytetrafluorethylene, which is known by a commercial name as Teflon ®.

Once the dough has been rolled to a predetermined thickness by the roller, a circular cutter is used to cut out disc-shaped pieces of dough from the rolled dough sample. The cutter edges and surfaces also are coated by polytetraflouroethylene. Preferably, five pieces of disc-shaped dough are cut, to provide a sufficient number of samples to ensure a reliable set of test results. The disc-shaped dough pieces are then placed upon resting trays, which resting trays are then placed into a chamber maintained at a predetermined temperature and humidity for a length of time sufficient for the dough to reach uniform conditions. The resting trays also are preferably coated with polytetrafluorethylene, the coating material having a commercial name of Teflon ®.

After the predetermined "resting" period has elapsed, each sample is in turn placed in the burst-testing portion of the apparatus. Here, air is introduced quickly initially, and then added slowly and steadily to stretch the sample disk. During this time, the air pressure inside the forming dough bubble is measured as a function of time, and also measured is the extension of the dough sample in terms of its changed surface area. At the bursting point of the dough sample, which bursts after expanding balloon-like into a semi-spherical membrane, the pressure suddenly drops to atmospheric pressure and the test ends. Doughs such as used for animal biscuits and the like burst more quickly and are less extensible than are doughs used, for example, for breads.

The testing is repeated until all of the dough samples have been tested. The properties of the dough are then calculated from the test measurements, and the values are averaged over all of the samples to determine the dough qualities of the dough batch.

Heretofore, it was assumed in the prior art that substantially all of the variability of the test results was due to the inherent limitations of the dough samples themselves and to the testing procedures. Heretofore also, no polytetrafluoroethylene coatings were used for the various components which contact the surface of the dough samples, as such were not necessary and since such were not believed heretofore to be relevant to the test results. By the present invention, an unexpected results occurs, namely that the reliability of the test results has been significantly increased. The statistical variability of the test results, defined as the standard deviation divided by the mean, is reduced by approximately one-half.

Further details and advantages of the present invention appear from the following description of a preferred embodiment shown schematically in the drawings.

BRIEF DESCRIPTION OF THE DRAWINGS

FIG. 5 is view illustrating a dough cut-out being tested;

FIG. 6 shows a set of curve results obtained from the testing operation, including test results from a plurality of samples;

FIG. 7 is a block diagram showing the method employed according to the present invention; and FIG. 8 is a side elevational view of dough being extruded onto a shelf.

DETAILED DESCRIPTION OF THE INVENTION

Figure 1:
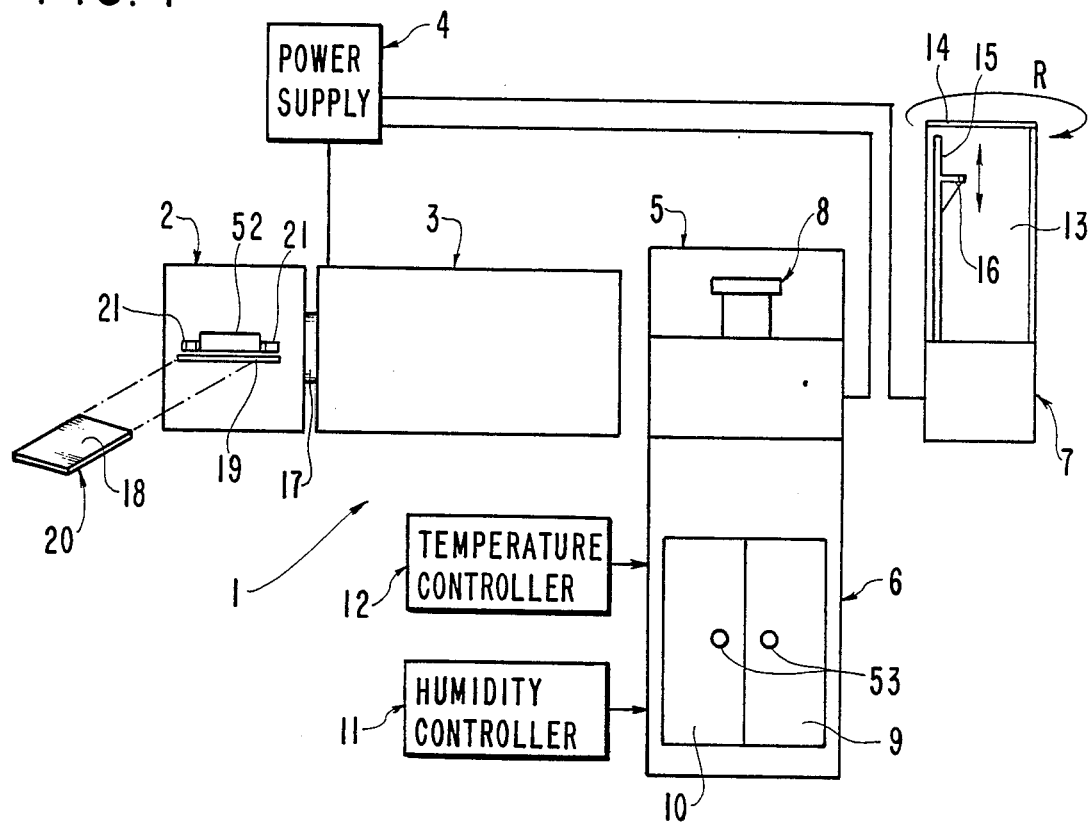
FIG. 1 shows a front view of an apparatus according the present invention.

FIG. 1 is a front elevational view of an Alveographe used in a preferred embodiment of the present invention. The apparatus 1 includes a dough mixer and extruder 2 having a motor and control system 3, which is linked to the mixer 2 by the shaft 17. The apparatus 1 includes a power supply 4 for supplying power to all of the operating components as illustrated in FIG. 1. The apparatus 1 includes the dough testing station 5 having an upstanding dough sample support 8.

The apparatus 1 includes a cabinet 6 having doors 9, 10. Each door has a knob 53. A humidity controller 11 and a temperature controller 12 are optionally provided to control humidity and temperature inside of the cabinet 6. The cabinet 6 is used for receiving samples of dough "resting", to permit the dough to come to a uniform temperature and humidity. An air pressure indicating output (not shown in the Figures) connects the test stand 5 with the graphical output device 7. The graphical output device 7 includes a cylindrical column 14 supporting a sheet of graph paper 13. A vertical post 15 movably supports a pen 16, the height of the pen 16 being dependent upon the air pressure supplied to the dough sample being stretched and ultimately burst. The cylinder 14 is adapted to rotate and does rotate so that during the upward and downward travel of the pen 16, rotation of the cylinder 14 brings different regions of the graph paper into contact with the pen 16. The upward and downward movement of the pen 16 is indicated by the double headed arrow in FIG. 1. The rotational movement of the cylinder 14 is indicated by the curved arrow R as seen in FIG. 1.

As seen in FIG. 1, a pair of headed members 21, 21 are connected to a support shelf 19. A receiving tray 20 is mountable adjacent to a slot 52 formed in the mixing chamber 2. The receiving tray 20 has an upper surface 18 which is composed of polytetrafluoroethylene according to the present invention.

The operation and nature of the Alveographe equipment is well-known in the food industry and a French book on the subject by Marcel Chopin, among many other references illustrating use and nature of this type of test equipment, is entitled *Cinquante Annees de Recherches Relatives Aux Bles et a Leur Utilisation Industrielle*, published in March of 1973 in Boulogne.

FIG. 8 is illustrative of the positioning of the receiving tray 20 atop the shelf 19, the tray 20 being retained snuggly against the shelf 19 by the heads of the numbers 21, 21. The top of the shelf 20 is adjacent and co-planar with the lower most edge of the slot 52 through which an extrudate 30 passes. The extrudate 30 is preferably a dough which has been mixed and blended inside of the mixer 2 until extrusion is desired.

Figure 2:
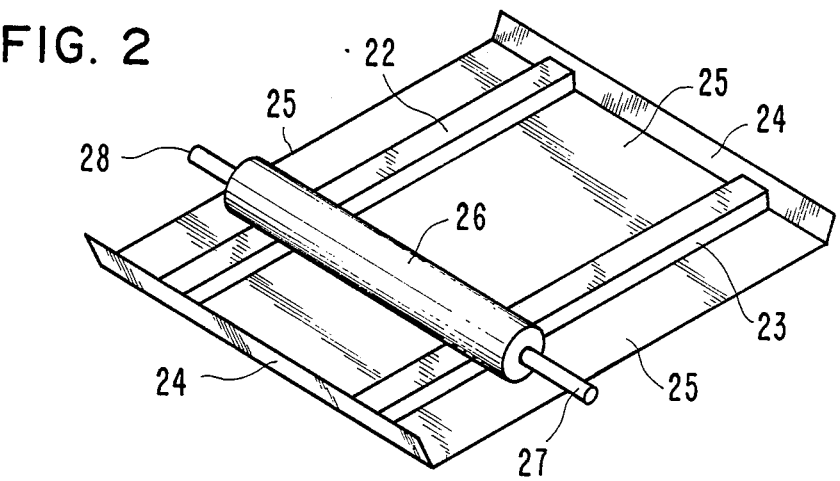
FIG. 2 is a perspective view showing a roller and rolling tray usable with the present invention.

A sheet 24, 25 is shown in FIG. 2. Prismatic rectangular bars 22, 23 are spaced in parallel relationship across the interior portion 25 of the cookie sheet 24. A rough sample would be rolled between prismatic rectangular bars 22, 23 by a rolling pin 26 having handles 27, 28. The thickness of each of the rectangular prismatic bars 22, 23 determines the thickness to which a dough sample 29 can be rolled. In a preferred embodiment, the cookie sheet 24 is formed of aluminum and has a Teflon ® coating. Nonetheless, any material for the cookie sheet 24 may be used, and any shape of cookie sheet 24 may be used. The rectangular prismatic bars 22, 23 may also be of any material, including wood, iron, steel, plastic, or the like, so long as they are strong enough to withstand breaking of substantial deformation during the rolling operation by roller 26.

The sheet 24, 25 shown in FIG. 2 is, according to the present invention, coated with a coating of polytetrafluoroethylene. The material known as polytetrafluoroethylene is commercially available under the name Teflon ®. Other coatings are also known employing such a non-stick surface or a low friction surface. The outer surface of the roller 26 is likewise coated, according to the present invention, with a coating of the material polytetrafluoroethylene. This material is known commercially as Teflon ®, among other commercial names. The extrudate 30 as shown in FIG. 8 is cut by a spatula or the like and placed above the tray 25, where the roller 26 is operated so as to reduce the thickness of the extrudate 30 to a generally uniform thickness, except around the edges of the extrudate 30. This is accomplished due to the predetermined thicknesses of the bars 22, 23 which cause a predetermined thickness to exist in the central regions of the extrudate dough 30.

Figure 3:
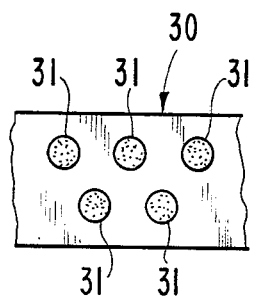
FIG. 3 is a top elevational view of a dough sheet with a circular cut-out formed therein.

Once the extrudate dough 30 has been rolled to a generally uniform thickness, a plurality of generally disk-shaped samples are cut into the dough, as seen in FIG. 3. The cutter is preferably any type of generally sharp-edges round cutter, such as a cookie-cutter or other circular, generally sharp-edged, object. The cutter, according to the present invention, also has a coating along its surfaces of polytetrafluorethylene. This material is known commercially as Teflon ®. Once the plurality of disk-shaped test samples 31 are cut, they are removed gently with a spatula, or alternatively the surrounding extrudate dough sheet 30 can be peeled off the sheet leaving the test disks 31 remaining lying upon the surface 25. An ordinary spatula or other article can be used to transfer the test disks 31 to a resting tray 40.

Figure 4:
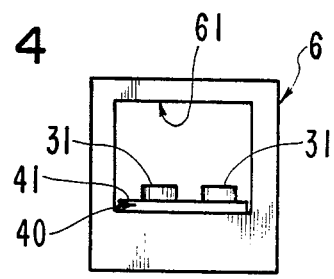
FIG. 4 is a front elevational view of the dough cut-outs lying upon a resting tray in a cabinet.

A resting tray 40 is shown in FIG. 4. This resting tray 40 preferably has an uppermost surface 41 composed of a coating of polytetrafluorethylene. The material forming the coating 41 is commercially available under the name Teflon ®. The test disks 31, 31 visible in FIG. 4 are seen resting atop the tray 40. The tray 40 is shown in FIG. 4 as being placed within the cabinet 6, having a resting chamber 61. The doors of the cabinets 6 are then closed, and the test disks 31 are permitted to reach an equilibrium temperature over a predetermined period of time, for example 15 minutes. After the test disks 31 have "rested" for a sufficient amount of time, they are then tested by being expanded under air pressure until bursting. This operation is as seen in FIG. 5.

In FIG. 5, the uppermost portion of the sample support block 8 is seen, with the lowermost portion being broken away. Here, the test disk 31 has been expanded by air pressure into a relatively thin membrane having a semi-spherical shape which is growing with a velocity W as indicated in the arrows in FIG. 5. During the entire time of expansion of the test sample 31, the air pressure within the support 8 is continuously measured and plotted with respect to time. Furthermore, the total amount of extension of the sample 31 is determined, either by direct measure, observation, or by theoretical calculations based upon the air pressure of the stand 8. This information is used to compute the extensibility of the sample 31 as well as to determine its maximum extension at bursting. This simulates the expansion of bubbles in materials such as breads and the like.

This is particularly useful for testing various strains of wheat, batches of flour, new recipes, or for comparing various combinations of ingredients. For example, doughs having a low amount of extensibility would include animal biscuits, crackers, and doughs for crusts. Dough having a high degree of extensibility, as measurable by the present test apparatus and method include bread doughs, cake doughs, and any other doughs in which expansion is highly desirable.

Tests results are indicated in FIG. 6, for a sample run of five tests. A horizontal reference line 80 and vertical reference line 81 have been drawn in. A plurality of curves, 82, each having a peak 83, result from the same mixed batch of dough each curve resulting from a different sample disk taken from that same sample of mixed dough. If the vertical reference line 81 is generally representative of the mean, the variability of the bursting points, indicated as generally vertical lines 84, indicate the bursting of each sample. Thus, a sample of dough having individual test disk which bursts at a relatively high degree of extension, may not be indicative of the quality of flour, or the dough sample used, and therefore, a large number of tests are highly desirable in order to ensure statistical accuracy when using the test results to compare one batch of dough against another batch of dough, or one flour versus other flours.

By the present invention, the variability of the test results is greatly reduced, and more closely approximates the "true" test results which would be achieved by running a far higher number of tests upon substantially identical doughs. This advantageous result, which occurs entirely due to the use of the coating material polytetrafluorethylene used upon the surfaces described, is unexpected since the coating material is not used at the point of testing itself, namely the stand 8. Therefore, it is unexpected that the use of the material polytetrafluorethylene would be of any value in conducting such tests. Such coatings were not heretofor employed in the dough testing art for burst testing.

An example of the effect of the coating of polytetrafluorethylene of the extrusion plate 20 the roller 26, the templates (not shown but described hereinabove), and resting chamber plate 40, are shown with respect to the Alveographe values. Here, the symbol P is a unit of pressure which is convertible into millimeters of mercury. This represents the pressure differential over atmospheric pressure during the test. The symbol L represents a link along the graph from the initial point at which air pressure is applied into the test sample, until the burst point or vertical line 84 is seen in FIG. 6. The symbol W represents the area under the curve formed for each sample in FIG. 6, which is indicative of the work applied to the four in extending it, and therefore is indicative of the strength of the flour or dough used. Extensibility is highly desirable in dough, as discussed above, and is indicative itself of the a higher degree of protein bonding, as well as of disulphide bonds.

The symbol X indicates the average or mean value of each of the above-described variables, which are summarized at the bottom of the table discussed hereinunder. The symbol S.D. is the standard variation of the various test samples about the mean. The symbol C.V. represents the coefficient of variation of the test samples about the mean. This is especially important in such testing, since a single batch of dough is expected to have a "true" value about which all of the other test results may vary. The coefficient of variation is a statistical variable well-known in the mathematical and statistical arts and sciences, and is readily calculated from the tabular value shown in Table 1 hereinunder. The left-hand columns represent the prior art test results and values, and the three right-hand columns represent the values taken during tests in accordance with the present invention, with coatings applied to the described surfaces.

TABLE 1

| Prior Art | | | Present Invention With Coatings | | |
|---|---|---|---|---|---|
| P | L | W | P | L | W |
| 57 | 92 | 185 | 56 | 75 | 160 |
| 56 | 77 | 160 | 55 | 86 | 180 |
| 57 | 76 | 160 | 56 | 88 | 165 |
| 56 | 93 | 180 | 57 | 85 | 175 |
| 61 | 83 | 185 | 56 | 85 | 170 |
| 59 | 69 | 155 | 57 | 80 | 165 |
| 57 | 80 | 165 | 59 | 81 | 175 |

TABLE 1-continued

| | Prior Art | | | Present Invention With Coatings | | |
|---|---|---|---|---|---|---|
| | P | L | W | P | L | W |
| | 59 | 75 | 160 | 57 | 83 | 160 |
| | 56 | 85 | 175 | 58 | 83 | 170 |
| X | 57.6 | 81.1 | 169.4 | 56.8 | 82.9 | 170 |
| S.D. | 1.64 | 7.5 | 11.2 | 1.13 | 3.6 | 5.8 |
| C.V. | 2.8 | 9.24 | 6.61 | 1.99 | 4.38 | 3.41 |

As can be seen from Table 1, the coefficient of variation (C.V.) for each of the values P, L, and W, is virtually halved with the present invention having coatings on the described surfaces, as compared to the prior art wherein such coatings are not present. This Table 1 represents actual test results taken under laboratory conditions with the same doughs and same flours being used for comparison with one another.

FIG. 7 is a block diagram illustrating the method of the present invention. At step 101, the dough ingredients are mixed and blended. At step 102, the mixed dough is extruded onto a sheet coated with polytetrafluoroethylene. At step 103, the extruded dough is cut into an appropriate sample size with the edge of a spatula.

At step 104, the dough sample which has been extruded is rolled to a predetermined thickness, using a roller and a support tray coated with polytetrafluoroethylene. Test disks are cut out from the rolled dough, using a cutter having surfaces coated with polytetrafluoroethylene, at the block 105.

At step 106, the test disks are placed upon a resting tray, which is also coated with polytetrafluoroethylene. The test disks are permitted to rest for a predetermined period of time as seen at step 107. At step 107, the resting tray rests within a chamber which preferably permits the test disks to reach a predetermined uniform temperature and any other desired stable conditions, for a predetermined period of time.

At step 109, each test disk is tested by employing air pressure and an Alveographe device to extend the dough biaxially to form a bubble-shaped structure which eventually bursts. During the entire testing procedure, the pressure of the air employed is carefully measured with respect to time, and a curve is made showing the air pressure and bursting points at which time the pressure drops to zero.

At step 109, the bursting test is repeated for N sample disks and after a desired number of sample disks have been tested from the same dough batch, a statistical analysis is performed to determine the dough extensibility, and other quantities associated with the particular dough sample employed.

The success of the present invention is not completely understood since as discussed in the above, there is no direct use of the coating of polytetrafluoroethylene in the actual bursting or test support portion 8. However, it is theoretically possible that the use of the coating of polytetraflouroethylene prevents minor surface defects from forming during the initial extrusion period, rolling period, cutting period, and resting periods, during which, to the naked eye, no such defects would be apparent. Also, alternatively, it is possible that the dough samples undergo some geometric or other changes during the above-described operations, some of which changes are inhibited slightly by the presence of the non-coated materials in the prior, but which changes are permitted to occur more repeatably by the apparatus according to the present invention. Nonetheless, the present invention is not dependent upon any particular theory of its operation, but relies upon the fact that it actually works and is used to dramatically and significantly reduce the variability of test results, and thereby increase the reliability of such test results. As seen from the sample tests shown in Table 1, the test results at the mean values X are very close between the prior art testing procedure and the procedure according to the present invention.

While a preferred embodiment has been shown and described, the scope of the present invention is not limited thereto, but is described by the following claims.

What is claimed is:

1. A method of improving the reliability of dough test results by reducing the variability in burst-testing type of apparatus and reducing the standard deviation of test results of a batch of dough by means of producing the samples to be tested using a process comprising the steps of:

forming a dough;

extruding samples of said dough onto a receiving tray;

rolling the dough samples to a uniform thickness;

resting the uniform thickness dough samples on a resting tray;

cutting the rested dough samples into uniform dough test samples, and testing said dough test samples in a burst testing type of apparatus and determining a parameter associated with dough extension as a function of time;

said improvement in dough test results being derived from a process of preparing more uniform dough test samples comprising:

extruding said dough samples onto a receiving tray having a low-friction coating thereon;

rolling said dough samples to a uniform thickness using a roller and a roller tray each having a low-friction coating thereon;

resting said uniform thickness dough samples on a resting tray having a low-friction coating thereon;

cutting said rested dough samples into uniform dough test samples using a cutter having a low-friction coating thereon and testing said uniform test samples in said burst testing type of apparatus and thereby get test results having a reduced variability and reduced standard deviation.

2. A method as claimed in claim 1 wherein burst-testing type of apparatus is an Alveograph.

3. A method as claimed in claim 1 wherein said low-friction coating is polytetrafluoroethylene.

4. An apparatus for preparing more uniform dough test samples for use in testing dough quality by reducing the variability in burst - testing type of apparatus and reducing the standard deviation of test results, said apparatus comprising:

a means for mixing dough;

a means for extruding the mixed dough;

a receiving tray for receiving the extruded dough, said receiving tray having a coating thereon which is a low-friction coating;

a rolling tray and a roller for rolling said extruded dough to a uniform thickness, said rolling tray having a coating thereon which is a low-friction coating, and said roller having a coating thereon which is a low-friction coating;

a resting tray for resting the dough thereon having a low-friction coating thereon and a resting chamber; and a forming implement having a low-friction coating thereon for forming dough test samples from said dough which has been rolled upon said rolling tray by said roller and rested in said resting trays;

whereby dough quality is reliably measured through biaxially extending said dough test samples in a burst testing type of apparatus; measuring a parameter associated with dough expansion and obtaining a low variability of test results upon dough samples taken from the same batch of dough.

5. The apparatus as claimed in claim 4 wherein said low-friction coating is composed of polytetrafluorethylene.

6. The apparatus as claimed in claim 4 wherein said burst-testing type of apparatus is an Alveographe.

7. The apparatus as claimed in claim 4 wherein each test sample is formed as a generally circular disk having a uniform thickness.

* * * * *